United States Patent [19]
Moretz et al.

[11] Patent Number: 5,210,882
[45] Date of Patent: May 18, 1993

[54] UNDERGARMENT WITH COMBINATION OF LOOSE FITTING SEAT, UPPER ABDOMEN AND LEG AREAS AND SUPPORTING CROTCH AREA

[76] Inventors: Herbert L. Moretz, 20205 Lola Cir., Davidson, N.C. 28036; Daniel L. Brier, 33 Angelfish Cay Dr., Key Largo, Fla. 33037

[21] Appl. No.: 842,224

[22] Filed: Feb. 26, 1992

Related U.S. Application Data

[63] Continuation-in-part of Ser. No. 791,066, Nov. 12, 1991.

[51] Int. Cl.⁵ .............................................. A41B 9/02
[52] U.S. Cl. .................................. 2/404; 2/400; 2/403; 2/401; 2/402; 2/406
[58] Field of Search .................. 2/400, 403, 402, 404, 2/406, 401; 602/70

[56] References Cited

U.S. PATENT DOCUMENTS

| | | | |
|---|---|---|---|
| 1,973,849 | 9/1934 | Erlanger | 2/404 |
| 2,191,169 | 2/1940 | Katz | 2/404 |
| 2,264,384 | 12/1941 | Kneibler | 128/159 |
| 2,328,087 | 8/1943 | McDonald | 128/159 |
| 2,384,165 | 9/1945 | Goldfarb et al. | 2/404 |
| 2,438,310 | 3/1948 | Ashe et al. | 2/224 |
| 2,486,499 | 11/1949 | Schoendorf | 2/224 |
| 2,494,261 | 1/1950 | Owenby | 2/404 |
| 2,624,336 | 1/1953 | Hansley | 128/159 |
| 2,641,257 | 6/1953 | Rutledge | 128/159 |
| 3,083,710 | 4/1963 | Rauser | 128/159 |
| 3,174,482 | 2/1965 | Parrott | 128/519 |
| 3,246,341 | 4/1966 | Paolucci | 2/224 |
| 3,511,234 | 5/1970 | Larson | 128/159 |
| 3,613,687 | 10/1971 | Kennedy | 2/406 |
| 3,706,103 | 12/1972 | Senser | 2/402 |
| 3,714,946 | 2/1973 | Rudes | 2/404 |
| 3,852,828 | 12/1974 | Silverstein | 2/401 |
| 4,067,068 | 1/1978 | Bregstein et al. | 2/406 |
| 4,351,340 | 9/1982 | McLeod | 2/406 |
| 4,555,245 | 11/1985 | Armbruster | 604/396 |
| 4,870,958 | 10/1989 | Webster | 128/159 |
| 4,880,424 | 11/1989 | Rautenberg | 2/401 |
| 4,961,419 | 10/1996 | Tribble | 602/70 |

FOREIGN PATENT DOCUMENTS

| | | | |
|---|---|---|---|
| 473454 | 5/1951 | Canada | 2/402 |
| 327823 | 8/1989 | European Pat. Off. | 2/401 |

*Primary Examiner*—Clifford D. Crowder
*Assistant Examiner*—Gloria Hale
*Attorney, Agent, or Firm*—W. Thad Adams, III

[57] ABSTRACT

An undergarment characterized by a loose comfortable fit in the seat, upper abdomen and leg areas and by a snug, supporting fit in the crotch area. The undergarment includes a relatively narrow expansible waistband component for encircling the waist of the wearer, a relatively loose, woven non-stretch fabric seat, upper abdomen and leg component attached to and carried by the waistband component for providing a loose, comfortable fit in the seat, upper abdomen and leg areas of the wearer and a relatively stretchable crotch component attached to and positioned in relation to the leg, upper abdomen and seat component to snugly support the crotch of the wearer. Embodiments are disclosed which include a multi-layer crotch with enhanced moisture management capacity and a crotch which includes a pouch for holding a separate moisture absorbing pouch.

7 Claims, 4 Drawing Sheets

UNDERGARMENT WITH COMBINATION OF LOOSE FITTING SEAT, UPPER ABDOMEN AND LEG AREAS AND SUPPORTING CROTCH AREA

TECHNICAL FIELD AND BACKGROUND OF THE INVENTION

This application is a continuation-in-part of application Ser. No. 791,066, filed on Nov. 12, 1991.

This invention relates to an undergarment with a combination of a loose fitting seat, upper abdomen and leg area and a snug, supporting crotch area. The undergarment combines the woven body of traditional boxer shorts with a knitted pouch, including fly panel of knitted briefs.

Generally, men choose to wear either boxer shorts of woven material or knitted briefs. Most men do not wear these styles interchangeably. Each style has certain advantages and disadvantages.

For example, boxer shorts have open, loose, relatively long legs and a full seat. Boxer shorts are woven of non-stretch fabric such as cotton or polyester/cotton blends. It is the fullness of the cut, not the fabric construction itself, which provides the comfort. Boxer shorts often gap open at the fly, and generally have only one thickness of cloth in the fly and crotch area. Boxer shorts also do not provide genital support, and have a center seam which extends under the crotch and up the back of the garment which can be uncomfortable.

Knitted briefs, on the other hand, have relatively tight, elasticized leg openings which fit up into the crotch rather than extending down the leg several inches. Briefs are also generally snug in the seat. The fly and the crotch area are generally a double-thickness of fabric. Since the fly is a double layer of fabric, it does not gap open.

Thus, for many men the boxer short is a more comfortable garment, but the fly which gaps, lack of support and reduced ability to absorb moisture are distinct disadvantages. The relative inability to absorb moisture is particularly difficult for those with minor urinary incontinence.

SUMMARY OF THE INVENTION

Therefore, it is an object of the invention to provide an undergarment which combines the advantages of both boxer shorts and briefs.

It is another object of the invention to provide an undergarment which provides roomy, loose and comfortable seat, upper abdomen and leg areas.

It is another object of the invention to provide an undergarment which provides a crotch area with snug support.

It is another object of the invention to provide an undergarment which provides a crotch area which includes provision for absorbing and holding moisture.

It is another object of the invention to provide an undergarment which provides the advantages of a boxer short without a center seam through the crotch and seat areas.

It is another object of the invention to provide an undergarment which provides the advantages of a boxer short without a single-thickness fly subject to opening. These and other objects of the present invention are achieved in the preferred embodiments disclosed below by providing an undergarment characterized by a loose comfortable fit in the seat, upper abdomen and leg areas and by a snug, supporting fit in the crotch area. The undergarment comprises a relatively narrow expansible waistband component for encircling the waist of the wearer, a relatively loose, woven non-stretch fabric seat, upper abdomen and leg component attached to and carried by the waistband component for providing a loose, comfortable fit in the seat, upper abdomen and leg areas of the wearer and a relatively stretchable crotch component attached to and positioned in relation to the leg, upper abdomen and seat component to snugly support the crotch of the wearer.

According to one preferred embodiment of the invention, the undergarment includes partially overlapping panels in the crotch component defining a fly.

According to another preferred embodiment of the invention, the crotch component is comprised of knitted fabric.

According to yet another preferred embodiment of the invention, the crotch component is comprised of stretch-woven fabric.

According to yet another preferred embodiment of the invention, the crotch component includes a multi-layer moisture absorbing panel for absorbing moisture and wicking it away from the skin of the wearer.

According to yet another preferred embodiment of the invention, the moisture absorbing panel comprises an inner hydrophobic fiber layer for being positioned next to the skin of the wearer, an intermediate hydrophilic fiber layer for wicking moisture from the inner hydrophobic fiber layer and away from the skin of the wearer, an outer hydrophilic fiber layer for trapping and holding moisture from the intermediate hydrophilic layer and a shell fabric defining the outermost layer of the crotch component.

Preferably, the inner hydrophobic fiber layer comprises brushed polyester, the intermediate hydrophilic fiber layer comprises hydrophilic nylon, and the outer hydrophilic fiber layer comprises brushed hydrophilic nylon.

According to one preferred embodiment of the invention, the moisture absorbing panel comprises an inner hydrophobic fiber layer for being positioned next to the skin of the wearer, an intermediate hydrophilic fiber layer for wicking moisture from the inner hydrophobic fiber layer and away from the skin of the wearer, an outer hydrophilic fiber layer for trapping and holding moisture from the intermediate hydrophilic layer, a hydrophilic membrane, and a shell fabric bonded to the hydrophilic membrane and defining the outermost layer of the crotch component. The shell fabric is permeable to air and moisture vapor flow and impermeable to liquid moisture passage.

According to one preferred embodiment of the invention, a pouch is positioned in the crotch component for receiving a separate moisture absorbent pad.

According to another preferred embodiment of the invention, the crotch component extends upwards to the waistband in the front of the undergarment, and/or upwards to the waistband in the rear of the undergarment.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
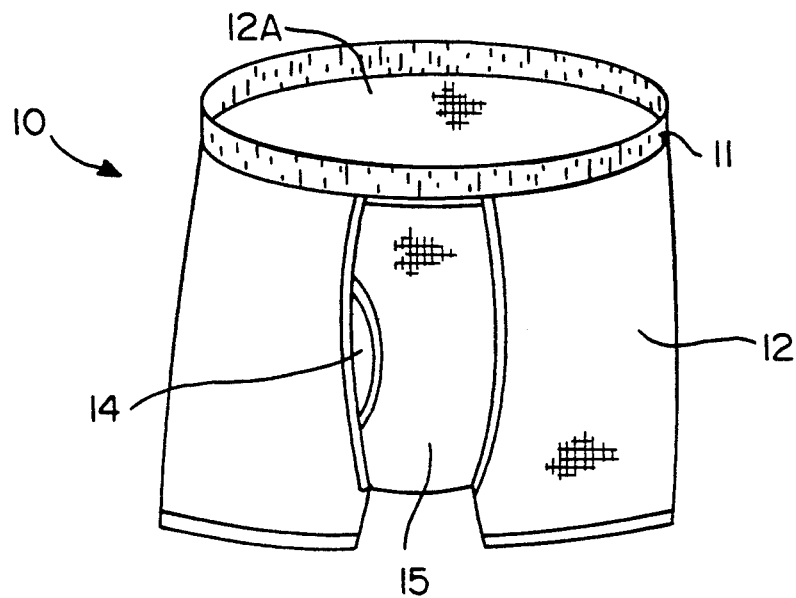
FIG. 1 is a front view of an undergarment according to one embodiment of the invention.

Referring now specifically to the drawings, an undergarment according to the present invention is illustrated in FIG. 1 and shown generally at reference numeral 10. Undergarment 10 is constructed of three types of components. Each of these types of components are or may be constructed of sub-components which are assembled in a conventional cut-and-sew operation to form the components which are then assembled into a completed garment.

Figure 2:
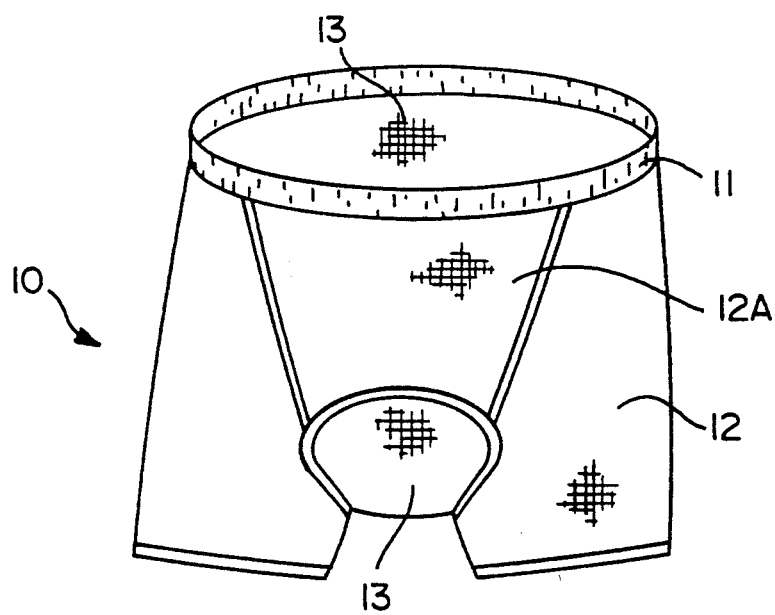
FIG. 2 is a rear view of an undergarment according to the embodiment of the invention as shown in FIG. 1.

The undergarment 10 includes a waistband 11 which is conventional and of the type typically incorporated into conventional woven boxer shorts. A relatively loose, woven non-stretch fabric seat, upper abdomen and leg component 12 is attached to and carried by the waistband component 11 by conventional cut-and-sew methods. The woven component 12 provides a loose, comfortable fit in the seat, upper abdomen and leg areas of the wearer typical of woven boxer shorts. As is shown in FIGS. 1 and 2, the woven component 12 may include a rear panel 12A. As is shown, rear panel 12A fits onto the waistband 11 and extends downwardly in the central portion of the seat of the undergarment and connects with the upper rear portion of a crotch component 13. This construction eliminates the center seam which is typical of conventional boxer shorts.

The relatively stretchable crotch component 13 is attached to and positioned in relation to the leg, upper abdomen and seat component 12 by conventional cut-and-sew methods to snugly support the crotch of the wearer. Crotch component 13 is fabricated to function as the crotch component of a pair of briefs. In other words, the crotch component 13 is a double layer of knitted fabric, for example, an 1×1 rib knit, which provides support to the crotch area of the wearer. The overlapping fabric layers define a fly area 14 which cannot gap open in the same way as the single layer fly of conventional boxer shorts.

The undergarment 10 in FIGS. 1 and 2 is for general wear by all ages according to size. However, even this construction is preferable for moisture control than conventional boxer shorts because of the double layer crotch component 13. The double layer crotch component 13 will acceptably absorb and permit evaporation of minimal amounts of moisture without discomfort to the wearer, and without leaking onto outer garments.

Figure 3:
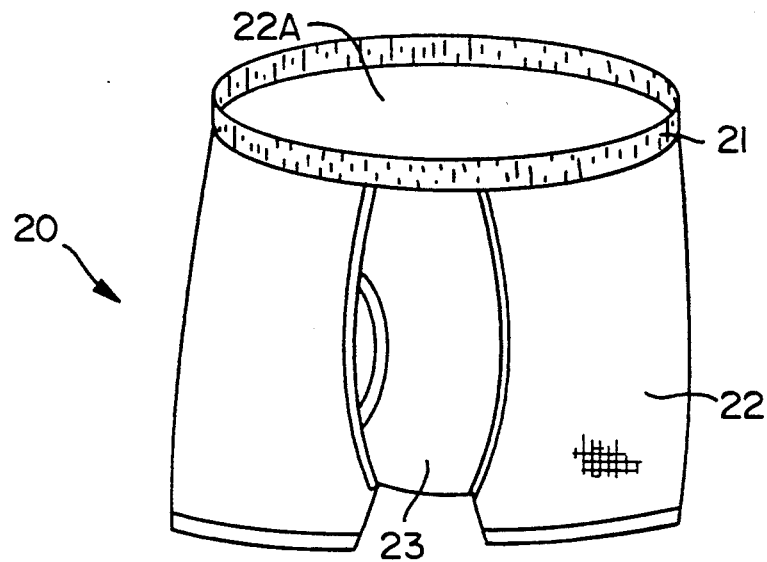
FIG. 3 is a front view of an undergarment according to another embodiment of the invention which includes a multi-layer moisture absorbent area.
Figure 4:
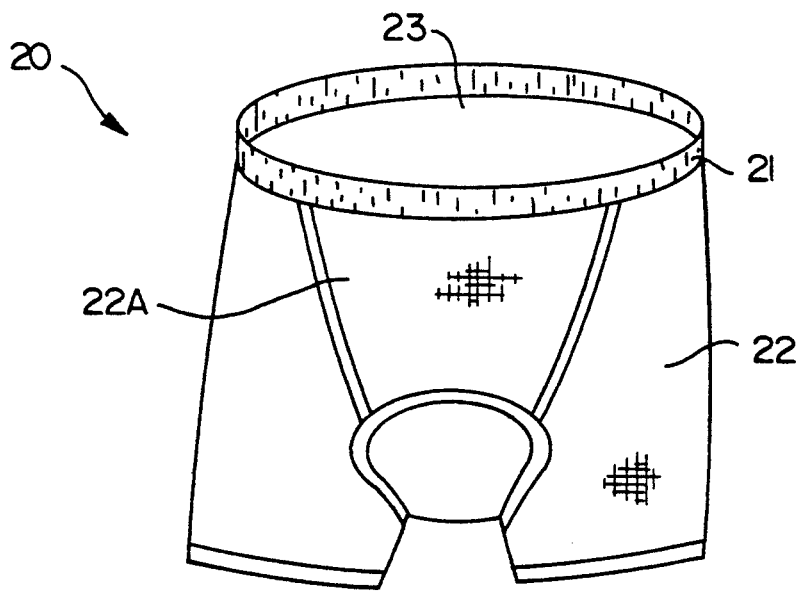
FIG. 4 is a rear view of an undergarment according to the embodiment of the invention as shown in FIG. 3.

Referring now to FIGS. 3 and 4, an undergarment 20 is shown which is adapted particularly for management of more than minimal amounts of moisture, such as may be present due to minor to moderate urinary incontinence. Undergarment 20 is constructed of three types of components. Each of these types of components are or may be constructed of sub-components which are assembled in a conventional cut-and-sew operation to form the components which are then assembled into a completed garment.

The undergarment 20 includes a waistband 21 which is conventional and of the type typically incorporated into conventional woven boxer shorts. A relatively loose, woven non-stretch fabric seat, upper abdomen and leg component 22 is attached to and carried by the waistband component 21 by conventional cut-and-sew methods. The woven component 22 provides a loose, comfortable fit in the seat, upper abdomen and leg areas of the wearer typical of woven boxer shorts. As is shown in FIGS. 3 and 4, the woven component 22 may include a rear panel 22A. As is shown, rear panel 22A fits onto the waistband 21 and extends downwardly in the central portion of the seat of the undergarment 20 and connects with the upper rear portion of a crotch component 23. This construction eliminates the center seam which is typical of conventional boxer shorts.

The relatively stretchable crotch component 23 is attached to and positioned in relation to the leg, upper abdomen and seat component 22 by conventional cut-and-sew methods to snugly support the crotch of the wearer. Crotch component 23 is fabricated to function as the crotch component of a pair of briefs. In other words, the crotch component 23 is a double layer of knitted fabric, for example, an 1×1 rib knit, which provides support to the crotch area of the wearer. The crotch component may also be constructed of stretch-woven fabric.

The overlapping fabric layers define a fly area 24 which cannot gap open in the same way as the single layer fly of conventional boxer shorts.

As is apparent from a comparison of FIGS. 1 and 2 with FIGS. 3 and 4, the undergarment 10 and undergarment 20 should be substantially indistinguishable from each other by appearance.

Figure 5:
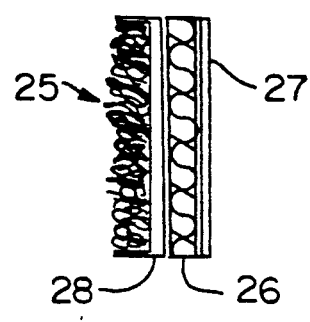
FIG. 5 is a cross-sectional view of one embodiment of the crotch area of the undergarment shown in FIGS. 3 and 4.
Figure 6:
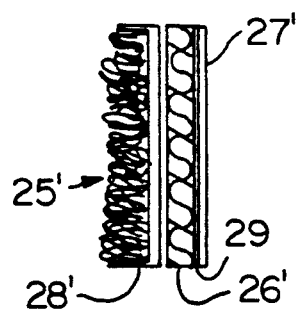
FIG. 6 is a cross-sectional view of another embodiment of the crotch area of the undergarment shown in FIGS. 3 and 4.

The fabric construction of the crotch component 23 is illustrated in cross-section according to two different embodiments in FIGS. 5 and 6.

Referring to FIG. 5, a hydrophobic layer 25 is intended to be next to and in contact with the skin of the garment wearer, with an outer hydrophilic layer 26 next to a shell fabric 27 from which the garment itself is constructed, as is illustrated in FIG. 3. An intermediate hydrophilic layer 28 wicks moisture away from the hydrophobic layer 25.

The hydrophobic layer 25 is constructed of a suitable non-absorbent fiber such as polyester. The adjacent hydrophilic layer 28 is formed of a highly absorbent fiber such as Hydrofil brand nylon fiber marketed by Allied Fibers. This fiber is characterized by a very low denier and results and a very supple, flexible and drapeable fabric. It has the strength, durability, ease of care and styling characteristics of nylon combined with absorbency somewhat better than cotton. The absorbency of this nylon is defined by its structure which permits moisture to be held on the greater surface area of the fibers and in the fabric interstices of fabrics woven with the low denier fibers. In contrast, cotton achieves its absorbency by taking the moisture into the fiber itself. Hydrofil nylon is a block copolymer of nylon 6 (approx. 85%) and polyethylene oxide diamine (approx. 15%)

and for this reason is referred to as a nylon even though it contains significant amounts of other material. The outer hydrophilic layer 26 of hydrophilic nylon is brushed to increase its bulk and moisture retaining ability.

An alternative construction is shown in FIG. 6. In this embodiment elements in common with FIG. 5 are shown with prime notation. A hydrophilic polyester membrane 29 may be bonded to the shell fabric 27' to act as a single fabric. A brushed hydrophilic nylon 26' resides interior to the polyester membrane 29. The hydrophobic layer 25' is constructed of non-absorbent fiber such as polyester, as described above. The adjacent hydrophilic layer 28' is formed of a highly absorbent fiber such as Hydrofil brand nylon fiber marketed by Allied Fibers, also as described above.

Figure 7:
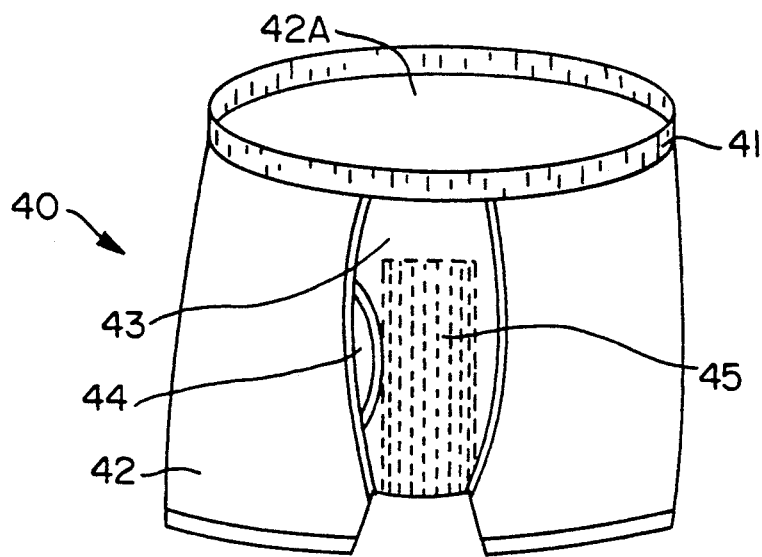
FIG. 7 is a front view of an undergarment according to another embodiment of the invention and including a pouch for a separate moisture absorbent pad.
Figure 8:
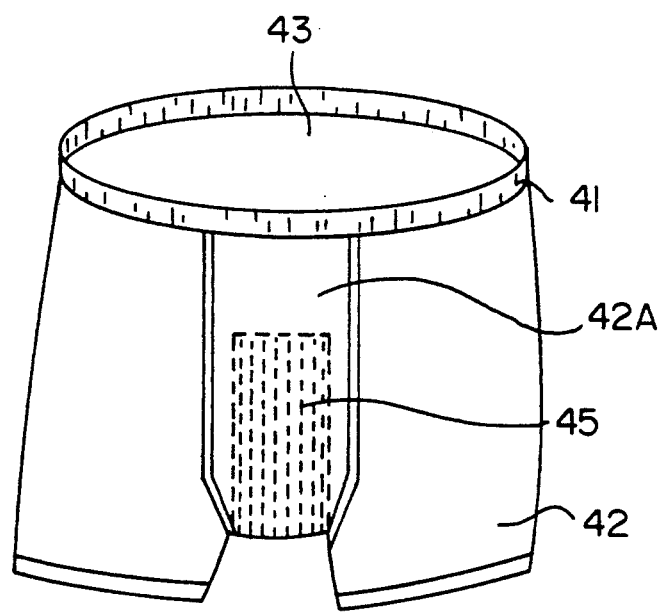
FIG. 8 is a rear view of an undergarment according to the embodiment of the invention as shown in FIG. 7.

Referring now to FIGS. 7 and 8, an undergarment 40 which includes a pouch in the crotch area is shown.

The undergarment 40 includes a waistband component 41 which is conventional and of the type typically incorporated into conventional woven boxer shorts. A relatively loose, woven non-stretch fabric seat, upper abdomen and leg component 42 is attached to and carried by the waistband component 41 by conventional cut-and-sew methods. The woven component 42 provides a loose, comfortable fit in the seat, upper abdomen and leg areas of the wearer typical of woven boxer shorts. As is shown in FIGS. 7 and 8, the woven component 42 may include a rear panel 42A. As is shown, rear panel 42A fits onto the waistband 41 and extends downwardly in the central portion of the seat of the undergarment 40 and connects with the upper rear portion of a crotch component 43. This construction eliminates the center seam which is typical of conventional boxer shorts.

The relatively stretchable crotch component 43 is attached to and positioned in relation to the leg, upper abdomen and seat component 42 by conventional cut-and-sew methods to snugly support the crotch of the wearer. Crotch component 43 is fabricated to function as the crotch component of a pair of briefs, including the provision of a fly 44.

In addition, a pouch 45 is sewn into the inside of the crotch 43, and is adapted to receive either a disposable or washable and reusable pad (not shown). The particular construction of the pouch 45 may include a pair of elongate lengths of fabric which sewn into the crotch component 43 from front to back and overlapping along the adjacent longitudinal inner edges. Other constructions are also possible. The crotch component may be of a knitted or stretch woven material so that it provides the type of support to the wearer typical of briefs.

An undergarment is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. An undergarment characterized by a loose comfortable fit in the seat, upper abdomen and leg areas and by a snug, supporting fit in the crotch area, said undergarment comprising:
   (a) a relatively narrow expansible waistband component for encircling the waist of the wearer;
   (b) a relatively loose, woven non-stretch fabric seat, upper abdomen and leg component attached to and carried by said waistband component for providing a loose, comfortable fit in the seat, upper abdomen and leg areas of the wearer;
   (c) a relatively stretchable crotch component attached to and positioned in relation to said leg, upper abdomen and seat component to snugly support the crotch of the wearer, wherein said crotch component includes a multi-layer moisture absorbing panel, said moisture absorbing panel comprising:
      (1) an inner hydrophobic fiber layer for being positioned next to the skin of the wearer;
      (2) an intermediate hydrophilic fiber layer for wicking moisture from said inner hydrophobic fiber layer and away from the skin of the wearer;
      (3) an outer hydrophilic fiber layer for trapping and holding moisture from said intermediate hydrophilic layer; and
      (4) a shell fabric defining the outermost layer of the crotch component.

2. An undergarment characterized by a loose comfortable fit in the seat, upper abdomen and leg areas and by a snug, supporting fit in the crotch area, said undergarment comprising;
   (a) a relatively narrow expansible waistband component for encircling the waist of the wearer;
   (b) a relatively loose, woven non-stretch fabric seat, upper abdomen and leg component attached to and carried by said waistband component for providing a loose, comfortable fit in the seat, upper abdomen and leg areas of the wearer;
   (c) a relatively stretchable crotch component attached to and positioned in relation to said leg, upper abdomen and seat component to snugly support the crotch of the wearer, wherein said crotch component includes a multi-layer moisture absorbing panel, said moisture absorbing panel comprising:
      (1) an inner hydrophobic fiber layer for being positioned next to the skin of the wearer;
      (2) an intermediate hydrophilic fiber layer for wicking moisture from said inner hydrophobic fiber layer and away from the skin of the wearer;
      (3) an outer hydrophilic fiber layer for trapping and holding moisture from said intermediate hydrophilic layer;
      (4) a hydrophilic membrane; and
      (5) a shell fabric bonded to said hydrophilic membrane and defining the outermost layer of the crotch component, said shell fabric permeable to air and moisture vapor flow and impermeable to liquid moisture passage.

3. An undergarment according to claim 1 or 2, and including partially overlapping panels in the crotch component defining a fly.

4. An undergarment according to claim 1 or 2, wherein said crotch component is comprised of knitted fabric.

5. An undergarment according to claim 1 or 2, wherein said inner hydrophobic fiber layer comprises brushed polyester, said intermediate hydrophilic fiber layer comprises hydrophilic nylon, and said outer hydrophilic fiber layer comprises brushed hydrophilic nylon.

6. An undergarment according to claim 1 or 2, and including a pouch positioned in said crotch component for receiving a separate moisture absorbent pad.

7. An undergarment according to claim 1 or 2, wherein said crotch component extends upwards to the waist in the front of the undergarment.

* * * * *